US008858417B2

(12) United States Patent
Khodak et al.

(10) Patent No.: US 8,858,417 B2
(45) Date of Patent: Oct. 14, 2014

(54) WARMING THERAPY DEVICE INCLUDING DUAL CHANNEL AIR CIRCULATION SYSTEM

(75) Inventors: Andrei Khodak, Hatfield, PA (US); Tobias Otte, Luebeck (DE)

(73) Assignee: Draeger Medical Systems, Inc., Telford, PA (US)

(*) Notice: Subject to any disclaimer, the term of this patent is extended or adjusted under 35 U.S.C. 154(b) by 608 days.

(21) Appl. No.: 13/062,423

(22) PCT Filed: Sep. 30, 2009

(86) PCT No.: PCT/US2009/058916
§ 371 (c)(1),
(2), (4) Date: Mar. 4, 2011

(87) PCT Pub. No.: WO2010/071705
PCT Pub. Date: Jun. 24, 2010

(65) Prior Publication Data
US 2011/0160521 A1    Jun. 30, 2011

Related U.S. Application Data

(60) Provisional application No. 61/122,874, filed on Dec. 16, 2008.

(51) Int. Cl.
*A61G 11/00* (2006.01)
*A61F 7/00* (2006.01)
*A61B 19/00* (2006.01)

(52) U.S. Cl.
CPC .............. *A61G 11/00* (2013.01); *A61G 11/005* (2013.01); *A61F 2007/006* (2013.01); *A61G 11/008* (2013.01); *A61B 2019/4868* (2013.01); *A61F 2007/0069* (2013.01)
USPC ........................................... 600/22

(58) Field of Classification Search
USPC ............ 600/21, 22; 128/845, 200.14, 205.26; 5/713, 710, 615, 644, 423, 694, 701
See application file for complete search history.

(56) References Cited

U.S. PATENT DOCUMENTS

| | | | | |
|---|---|---|---|---|
| 4,876,773 A * | 10/1989 | Wade | | 27/23.1 |
| 5,730,355 A | 3/1998 | Lessard et al. | | 237/3 |
| 5,800,335 A * | 9/1998 | Koch et al. | | 600/22 |
| 5,935,055 A | 8/1999 | Koch et al. | | 600/22 |
| 6,270,452 B1 * | 8/2001 | Donnelly et al. | | 600/22 |
| 2005/0086739 A1* | 4/2005 | Wu | | 5/423 |
| 2008/0076961 A1 | 3/2008 | Kuo et al. | | 600/22 |
| 2008/0125619 A1 | 5/2008 | Otte et al. | | 600/22 |

(Continued)

FOREIGN PATENT DOCUMENTS

| | | | | |
|---|---|---|---|---|
| DE | 100 30 399 A1 | 1/1992 | | F24F 7/00 |
| DE | 198 05 654 A1 | 8/1999 | | A61G 11/00 |

(Continued)

*Primary Examiner* — Christine Matthews
(74) *Attorney, Agent, or Firm* — DLA Piper LLP (US)

(57) ABSTRACT

An apparatus and method for performing warming therapy is described. In one exemplary embodiment, the apparatus includes a patient support assembly and an air circulation system coupled to the patient support assembly, which includes first and second air flow channels which are separate from one another. The first and second air flow channels may be separately activated, depending upon the air flow required. Additionally, the elements of the air circulation system are easily disassembled, so as to allow easy cleaning of the system which, in turn, maintains a sterile patient environment.

16 Claims, 9 Drawing Sheets

(56) References Cited

U.S. PATENT DOCUMENTS

2008/0234538 A1 9/2008 Lehnhaeuser .................. 600/22
2008/0263775 A1* 10/2008 Clenet .............................. 5/694
2009/0217923 A1* 9/2009 Boehm et al. ............ 128/200.14

FOREIGN PATENT DOCUMENTS

| EP | 0 088 704 A1 | 9/1983 | ............. A61G 11/00 |
| EP | 0 656 183 A2 | 6/1995 | ............. A47C 20/08 |
| WO | 2008/142650 A1 | 11/2008 | ................ A61F 7/00 |

* cited by examiner

WARMING THERAPY DEVICE INCLUDING DUAL CHANNEL AIR CIRCULATION SYSTEM

CROSS-REFERENCE TO RELATED APPLICATIONS

This application is a of International Application No. PCT/US09/58916, filed Sep. 30, 2009 (WO 2010/071705, published Jun. 24, 2010), which claims priority to U.S. Provisional Application Ser. No. 61/122,874, filed Dec. 16, 2008, the entire contents of which are hereby incorporated by reference, as if fully set forth herein.

FIELD OF THE INVENTION

This present invention relates generally to a method and apparatus for performing warming therapy on medical patients. More particularly, the present invention relates to a method and apparatus for circulating air within an enclosure for a medical patient which provides improved air flow, and which includes an apparatus which may be easily disassembled and cleaned for maintaining a sterile environment for the medical patient.

BACKGROUND OF THE INVENTION

Many conventional warming therapy devices (e.g., incubators, warmers, etc.) include some type of air circulation system. Typically, the air circulation system is used for moving heated, humidified air into and out of a space surrounding a patient. For example, in a typical 'closed care' environment the patient may be covered by a hood or other member which assists in maintaining a desired temperature and humidity around the patient. In such a setting, air circulation systems are used to move heated, humidified air across the patient, in order to maintain a desired patient temperature and reduce the water loss.

For example, U.S. Pat. No. 5,935,055, the disclosure of which is hereby incorporated by reference in this application, as if fully set forth herein, shows a conventional warming therapy device including a lying surface 1 for a patient, and a housing 8 (i.e., hood) for surrounding the patient. Also included are a fan 4 and electric drive motor 5 for rotating the fan. A circular air heater 6 surrounds the fan 4 and operates to heat the air inside the housing 8. In particular, heated air is blown by the fan 4 to first and second nozzles 11 (as shown by the directional arrows in FIG. 2), where it is transmitted into the upper part of the housing 8 through parallel slots 7 which run along the two long sides of the housing. Exhaust slots 9 are provided along the two short sides of the housing 8 for collecting the air transmitted to the upper portion of the housing, and for returning such air to the area around the fan 4.

U.S. Pat. No. 5,730,355, the disclosure of which is hereby incorporated by reference into this application, discusses an incubator in which an air curtain is formed when one of first and second access doors 12, 20 of a hood 10 are opened, in order to maintain the temperature and environment within the hood. In particular, the incubator includes openings 24, 26 through which air passes into the area of the hood 10. When one of the access doors 12, 20 is opened, the temperature of a heater 32, and the speed of a fan 36, are increased to create an air curtain across the open access door, and compensate for temperature losses through the open access door.

U.S. Pat. No. 6,270,452, the disclosure of which is hereby incorporated by reference into this application, discusses an air circulation system for a warming therapy device. The warming therapy device 1 includes a head end 5a, a foot end 5b, and lateral sides 5c, 5d. The lateral sides 5c, 5d and the foot end 5b include slots 37 from which air emanates forming air curtains 20-22 and 23-25. The head end 5a includes an intake 63 (i.e., air return nozzle) which collects the air emanating from the slots 37 and returns it to an air circulation system.

Finally, US Pat. Pub. No. 2008/0234538, the disclosure of which is hereby incorporated by reference into this application, discusses an air circulation system for a warming therapy device. The warming therapy device 1 includes two lengthwise sides 2, a head side 3, and a foot side 4. The lengthwise sides 2 and the foot side 4 include air supply means 7,8, respectively. The head side 3 includes a front wall 10 in which is disposed an exhaust means 9 (i.e., air return). In operation, air which exits the lengthwise and foot side air supply means 7, 8 is blown toward the exhaust means 9, where it is collected and re-circulated.

However, air circulation systems of conventional warming therapy devices (such as the ones discussed above) often times cannot maintain a desired humidity level in the microenvironment around the patient if an access portal (e.g., hand port, hood) is opened. Additionally, such conventional devices are often difficult to clean, due to the way in which they are integrated into the warming therapy devices. For example, the air flow ducts for conventional air circulation systems are often built into the base of the respective warming therapy device, and thus are difficult (and sometimes impossible) to disassemble and clean. Because one of the objectives of a warming therapy device is to create a sterile and hygienically sound environment for the patient, an air circulation system which may be easily disassembled and cleaned is highly desirable.

Accordingly, there is presently a need for a warming therapy device that includes an air circulation system which can maintain a desired humidity in open care configurations (e.g., where a hand port or the hood is open) may be easily disassembled and cleaned, but which also maintains a high rate of air flow through the device.

SUMMARY OF THE INVENTION

An exemplary embodiment of the present invention comprises an apparatus including a patient support assembly and an air circulation system coupled to the patient support assembly, the air circulation system including first and second air flow channels which are separate from one another.

An exemplary embodiment of the present invention also comprises an apparatus including a patient support assembly and a mattress tray assembly coupled to the patient support assembly, wherein the mattress tray assembly includes an air circulation system coupled to the patient support assembly, the air circulation system including first and second air flow channels which are separate from one another.

An exemplary embodiment of the present invention also comprises a method of providing warming therapy to a patient, the method including steps of providing an air circulation system in proximity to a patient, the air circulation system including first and second air flow channels which are separate from one another, providing at least one heater adjacent the air circulation system and activating the first air flow channel using at least one first fan device, such that air flows through the first air flow channel, is heated by the at least one heater, and is supplied to the patient.

DETAILED DESCRIPTION

The present invention relates to a warming therapy device (e.g., incubator, warmer, etc.) including an air circulation system which is more efficient than prior systems, and which allows easy cleaning of the system. In particular, the warming therapy device includes a mattress tray assembly with an air circulation system formed of various component parts which may be easily assembled and disassembled for cleaning purposes. The air circulation system preferably includes at least one nozzle for assisting in the circulation of air through the mattress tray assembly.

Conventional warming therapy devices circulate air through vents disposed around the edges of the mattress on which the infant patient rests. The present invention provides for a more efficient and effective method of circulating air within a warming therapy device by implementing at least one nozzle above the mattress at one end of the warming therapy device. In particular, the warming therapy device according to the exemplary embodiments of the present invention includes at least one nozzle for collecting air within an incubation chamber, and feeding it through an air circulation system (including a fan) and back into the incubation chamber. Another advantage of the present invention is reduction in size. Particularly, the distance from one or more sides of the warming therapy device to the edge of the mattress is decreased. Yet another advantage is the ease of cleaning the warming therapy device as compared to conventional devices. In particular, all air ducts in the warming therapy device can be easily opened without use of tools, so all inside surfaces of the air ducts are directly accessible for cleaning.

Closed care warming therapy devices (e.g., incubators) provide physical separation between the environment where the infant patient is disposed and the surrounding ambient air. This separation is typically provided by a hood or similar member, which encloses the infant patient therein. This encapsulation of the infant patient facilitates creation of conditions favorable for the infant patient's development. Often times, the conditions inside the hood can be significantly different from those present in the ambient environment. Conditions inside the hood may be determined by varying the temperature level, humidity and/or oxygen concentration within the closed care environment, all of which can be controlled automatically using sensors integrated in the warming therapy device. For example, the temperature within the closed care environment may be controlled by sensing the skin temperature of the infant patient and making appropriate adjustments.

Alternatively to closed care warming therapy devices, open care devices (e.g., heaters or warmers) supply heat (through, e.g., overhead infrared radiation) to the infant patient to promote development, and do not typically utilize a hood which separates the infant patient from the surrounding environment. The amount of heat supplied to the infant patient may be fixed, or controlled by one or more skin temperature sensors coupled to the patient, as noted above.

Figure 1:
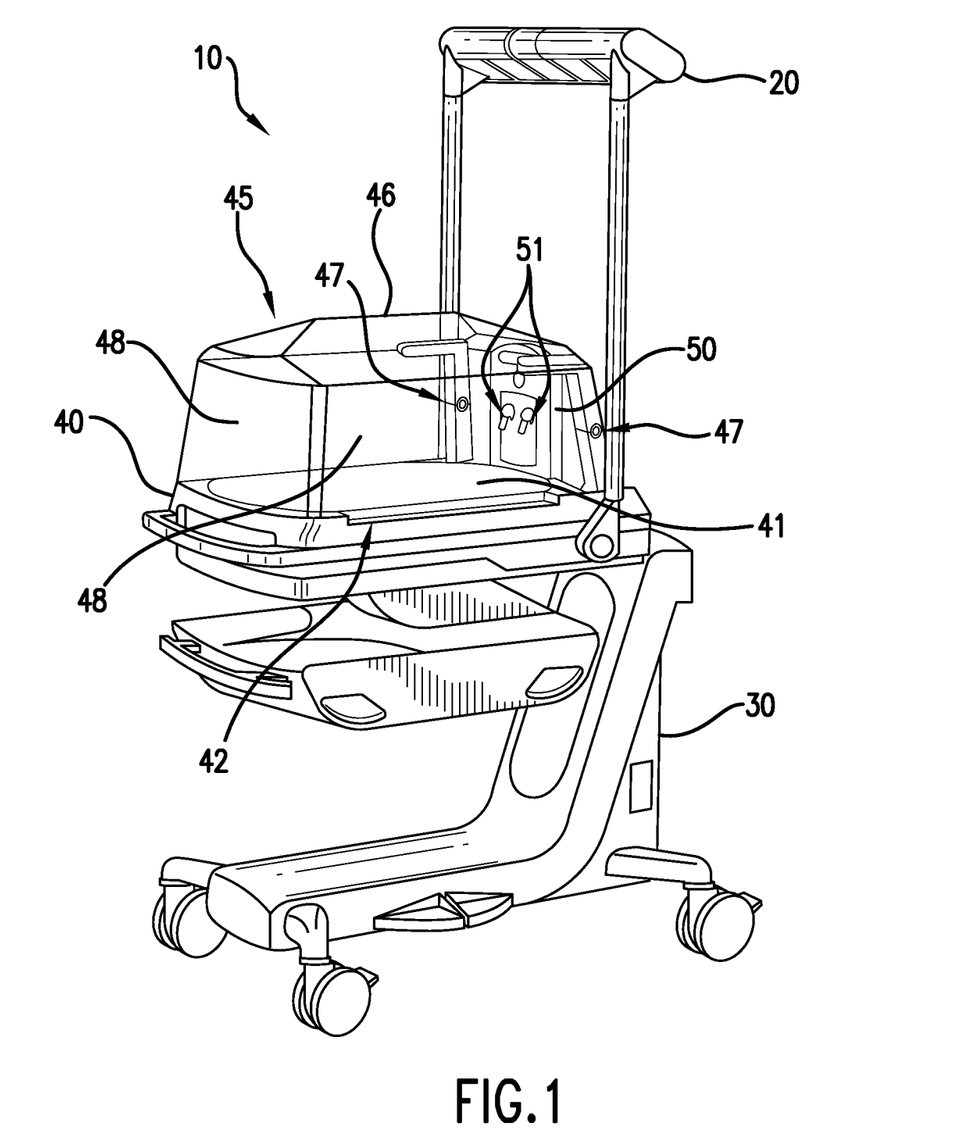
FIG. 1 is perspective view of a warming therapy device according to a first exemplary embodiment of the present invention.
Figure 2:
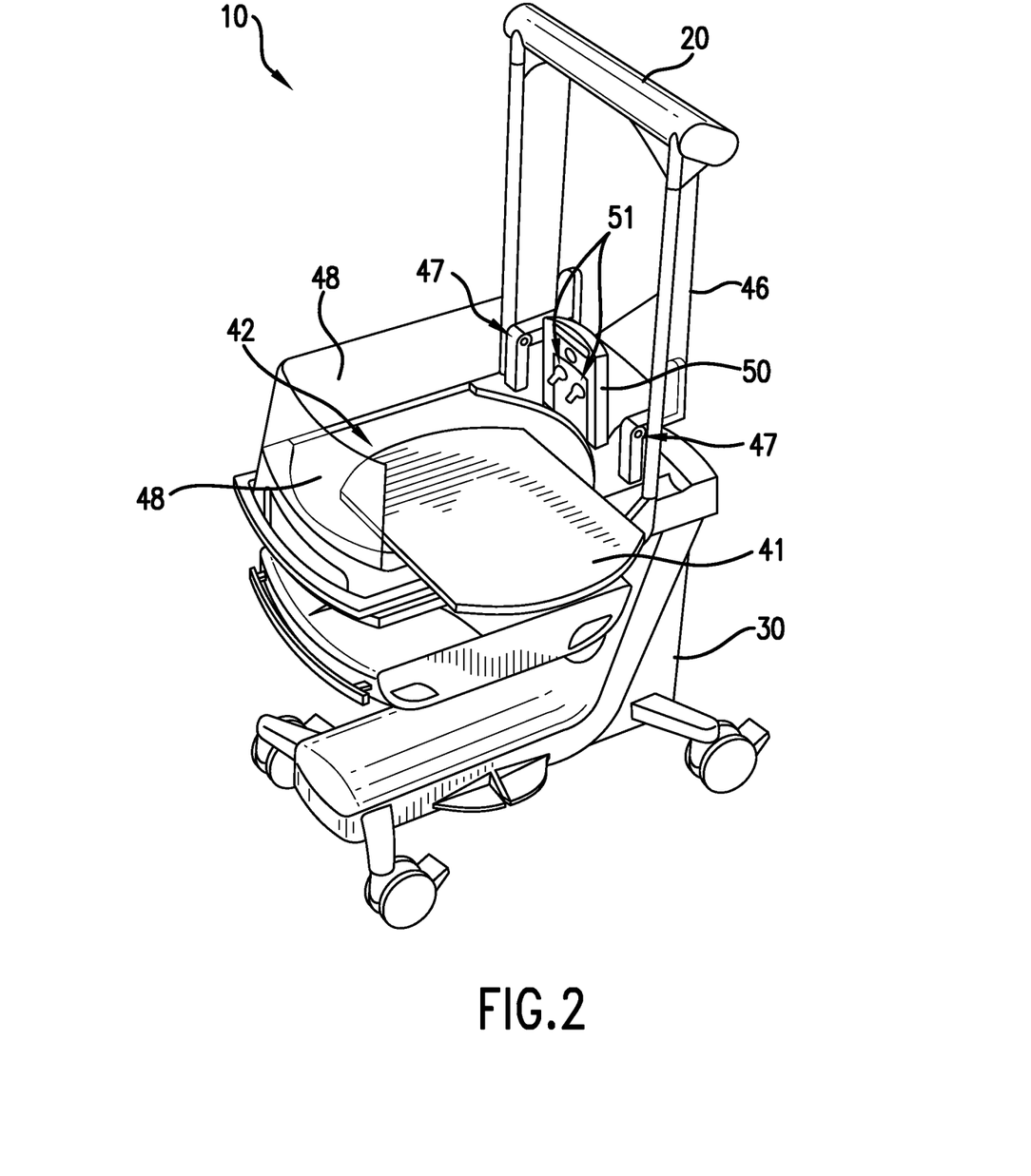
FIG. 2 is an overhead perspective view of the warming therapy device of FIG. 1.

Flexible care warming therapy devices allow simultaneous creation of a separate environment (i.e., inside the hood, when the hood is closed), which can provide humidity, and heating of the infant patient in the warming therapy device (i.e., when the hood is open). Thus, flexible care devices can operate as either 'open care' or 'closed care' devices. FIGS. 1 and 2, discussed below, show a flexible care warming therapy device according to a first exemplary embodiment of the present invention.

FIGS. 1 and 2 show a warming therapy device 10 according to a first exemplary embodiment of the present invention. The warming therapy device 10 includes a radiant heater head 20, and a patient support assembly 30 including a mattress tray assembly 40. The mattress tray assembly 40 may include a hood 45 which has a top portion 46 which pivots about one or more axes 47. The hood 45 may also include one or more sidewalls 48 which may be slideable, removable, pivotable or rotatable. The mattress tray assembly 40 also preferably includes a mattress tray 42, with a mattress 41 disposed therein. The warming therapy device 10 may optionally include a backplane 50, to which ventilation hoses and other devices may be coupled through, for example, interconnection nozzles 51.

FIG. 2 shows the top portion 46 of the hood 45 rotated up so that it is approximately ninety degrees (90°) with respect to the mattress tray 42. In the exemplary embodiment, the sidewalls 48 of the hood 45 are capable of sliding vertically within a portion of the mattress tray assembly 40, so that they may become disposed, partially or completely, below the plane of the mattress tray 42, or removed completely. In the exemplary embodiment shown in FIG. 2, the front sidewall 48 has been removed to permit movement of the mattress tray 42 in a direction away from the warming therapy device 10.

When the hood of a flexible care device (such as the warming therapy device 10 described above) is partially opened, such as, for example, when one or more of the sidewalls 48 are opened, removed or adjusted, the microenvironment (i.e., the environment created inside the hood 45) may begin to deteriorate due to the buoyancy of the warmed, humidified air contained therein. To prevent such deterioration, some conventional devices create 'air curtains' along the walls of the device when one or more of the sidewalls are opened, removed or adjusted. The air curtains may generate a spatial volume separation between the microenvironment and the ambient environment, and generally comprise jets of warm, humidified air flow through slots or openings along the walls of the device. The stability of the environment created by the air curtains is determined, in part, by the parameters of the air passing through the slots or openings (e.g., velocity, turbulence intensity, density). In general, the initial velocity of air emanating from the jet must be higher along the sidewalls, which have been opened, removed or adjusted, than in the closed care state of the device.

Activation of air curtains can be achieved using electrical switches connected to the sidewalls (e.g., door open/close sensors), or by physical opening of the jet nozzles disposed along the periphery of the device by the caregiver. When using electrical switches and sensors, the power of the fans, heaters and humidifiers coupled thereto may be controlled according to needed parameters.

Air circulation systems which utilize air curtains may also include an air return unit which creates a pressure sink, and hence adds dynamic stability to the microenvironment and the air curtains. In some cases, the air return unit may be disposed on one side of the warming therapy device (e.g., the side closest to the head of the infant patient), and the air curtain jets may be disposed on other sides of the device (e.g., the sides to the left and right of the infant patient, as well as the side closest to the feet of the infant patient). In order to maintain a stable environment when one or more of the sidewalls of the warming therapy device are opened, and to keep high efficiency for the device, such air circulation systems using air curtains should constantly assess the state of the device, and react accordingly.

Air circulation systems including air curtains can be used not only in closed care devices (e.g., incubators), but also in open care and flexible care devices. As noted above, in open care, the hood is removed or opened and the infant patient is heated by overhead infrared radiation. In such a case, air curtains may still be formed along the sides of the device to supply warm humidified air to the area surrounding the infant patient. For example, an opening or nozzle at the foot end of the mattress may supply warm, humidified air, and a return at the head end of the mattress may receive such air, thereby creating an air curtain over the patient. Additional air curtains may be formed on the left and right sides of the mattress to prevent the entrainment of colder, ambient air to the patient. In such a case, the foot-end nozzle parameters (e.g., velocity), geometry and discharge angle may be optimized to achieve optimal propagation to the head-end return unit, and thereby reduce the spread of the air from the nozzle, and mixture of such air with the ambient air.

Figure 3:
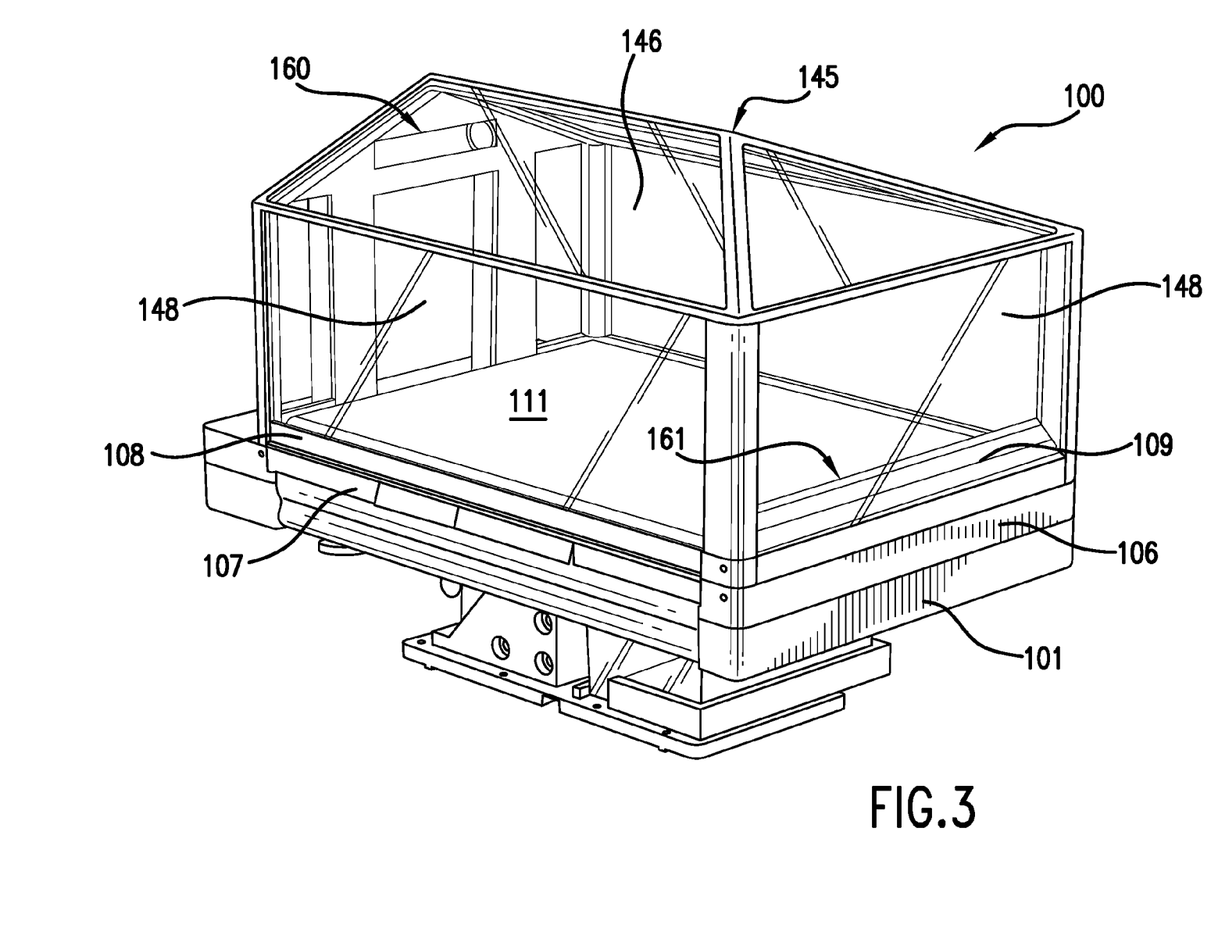
FIG. 3 is a perspective view of a mattress tray assembly according to a first exemplary embodiment of the present invention.

FIG. 3 shows a perspective view of a mattress tray assembly 100 according to a first exemplary embodiment of the present invention. The mattress tray assembly 100 may be used, for example, in place of the mattress tray assembly 40 in the warming therapy device 10 shown in FIGS. 1 and 2. The mattress tray assembly 100 includes a hood 145, formed of a top portion 146, and one or more sidewalls 148 which may be slideable, removable, pivotable or rotatable. The mattress tray assembly 100 may also include a mattress tray 108, with a mattress 111 disposed therein. The mattress tray assembly 100 may additionally include a first nozzle 160 disposed under the hood 145 and overlying the mattress tray 108 which acts as an air return. A second nozzle 161 may optionally be disposed at an opposing end of the mattress tray assembly 100 from the first nozzle 160, and may include an air control device 109 to open and close an air passage to thereby enable and disable air flow through the second nozzle 161. For example, the first nozzle 160 may be disposed at a head-end of the mattress tray assembly 100, and the second nozzle 161 may be disposed at a foot-end of the mattress tray assembly.

The mattress tray assembly 100 may also include a base member 101, a base cover 106, an X-ray cassette tray 107, and an air control device 109, as shown in more detail in FIG. 4 discussed below. The configuration of the base member 101 is such that air flow passages are created along the long sides thereof (i.e., the left and right sides of the mattress tray assembly 100). These air flow passages, which are explained further below, provide a point of entry for air into the chamber created under the hood 145. These air flow passages, along with the first and second nozzles 160, 161, and first and second fan devices 102, 103 described below (in connection with FIG. 4), form the basic elements of an air circulation system.

The air control device 109 may comprise a flap or other equivalent means, which may be opened and closed so as to allow air to flow through the second nozzle 161. For example, when the air control device 109 is disposed in a 'closed' position, the nozzle 161 will not be active, but when the air control device is disposed in an 'open' position, the nozzle 161 is active. As explained below, when the air control device 109 is disposed in the 'open' position air is directed from the second nozzle 161 towards the first nozzle 160. This direction of air flow from the second nozzle 161 back towards the first nozzle 160, improves the efficiency of air flow through the air circulation system.

Figure 4:
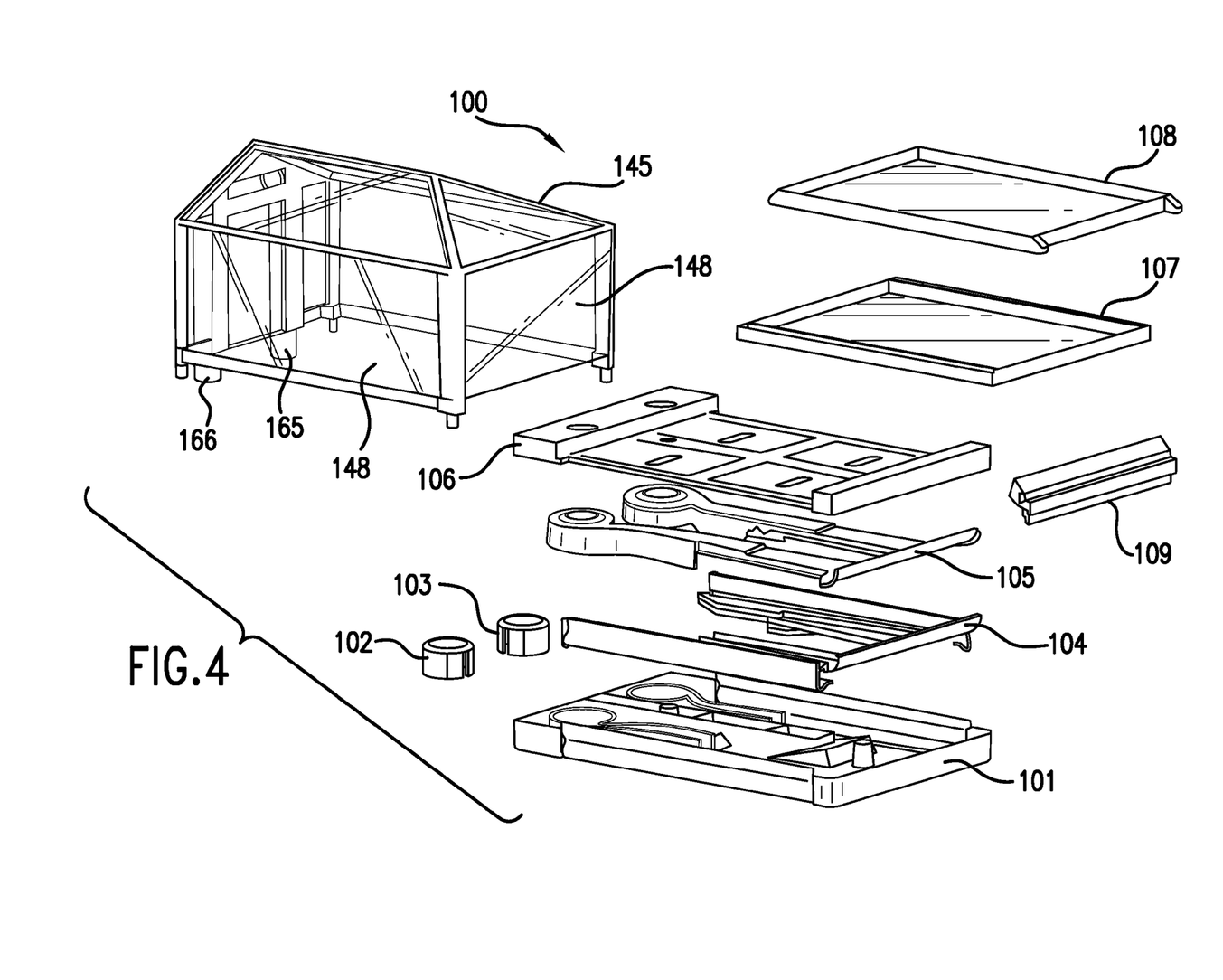
FIG. 4 is an exploded perspective view of the mattress tray assembly shown in FIG. 3.
Figure 9A:
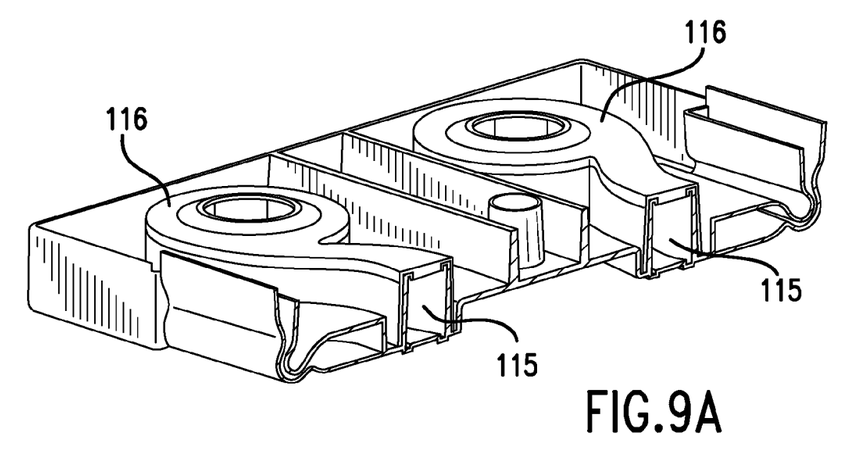
FIG. 9A is a perspective view of the mattress base and second circulation member shown in FIG. 4.
Figure 9B:
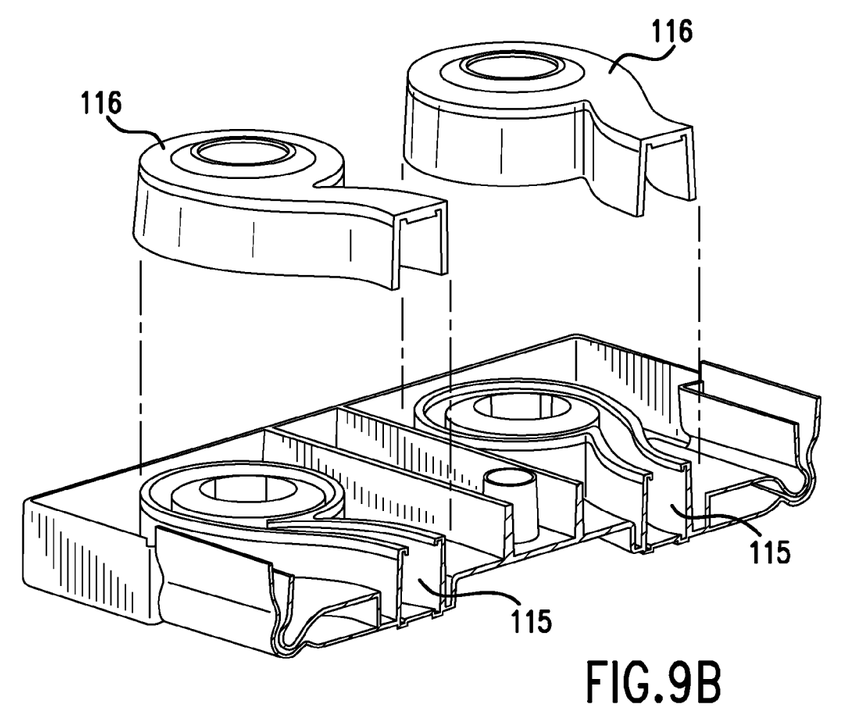
FIG. 9B is a perspective exploded view of the mattress base and second circulation member shown in FIG. 4.

FIG. 4 shows an exploded perspective view of the mattress tray assembly 100. In the exploded view, the various component elements of the mattress tray assembly 100 are shown, including the base member 101, first and second fan devices 102, 103, a first air circulation member 104, a second air circulation member 105, the base cover 106, the X-ray cassette tray 107, the mattress tray 108 and the air control device 109. All of the elements described above can be easily removed from the mattress tray assembly 100, which makes for easy cleaning of the separate elements. For example, when cleaning the air circulation system, the mattress tray 108 may be removed first, then the X-ray cassette tray 107, and then the base cover 106 and air control device 109. At this point, the second air circulation member 105 may be removed to expose the first and second fan devices 102, 103 (as shown in FIGS. 9A and 9B), which may also be removed for cleaning. The first air circulation member 104 may also be removed to permit cleaning of the air flow channels 182, 183 (shown specifically in FIGS. 5 and 6) formed in the base member 101. Once all the elements have been cleaned, they can be easily placed back together in reverse order, so that the mattress tray assembly may again be used for supporting a patient.

Figure 5:
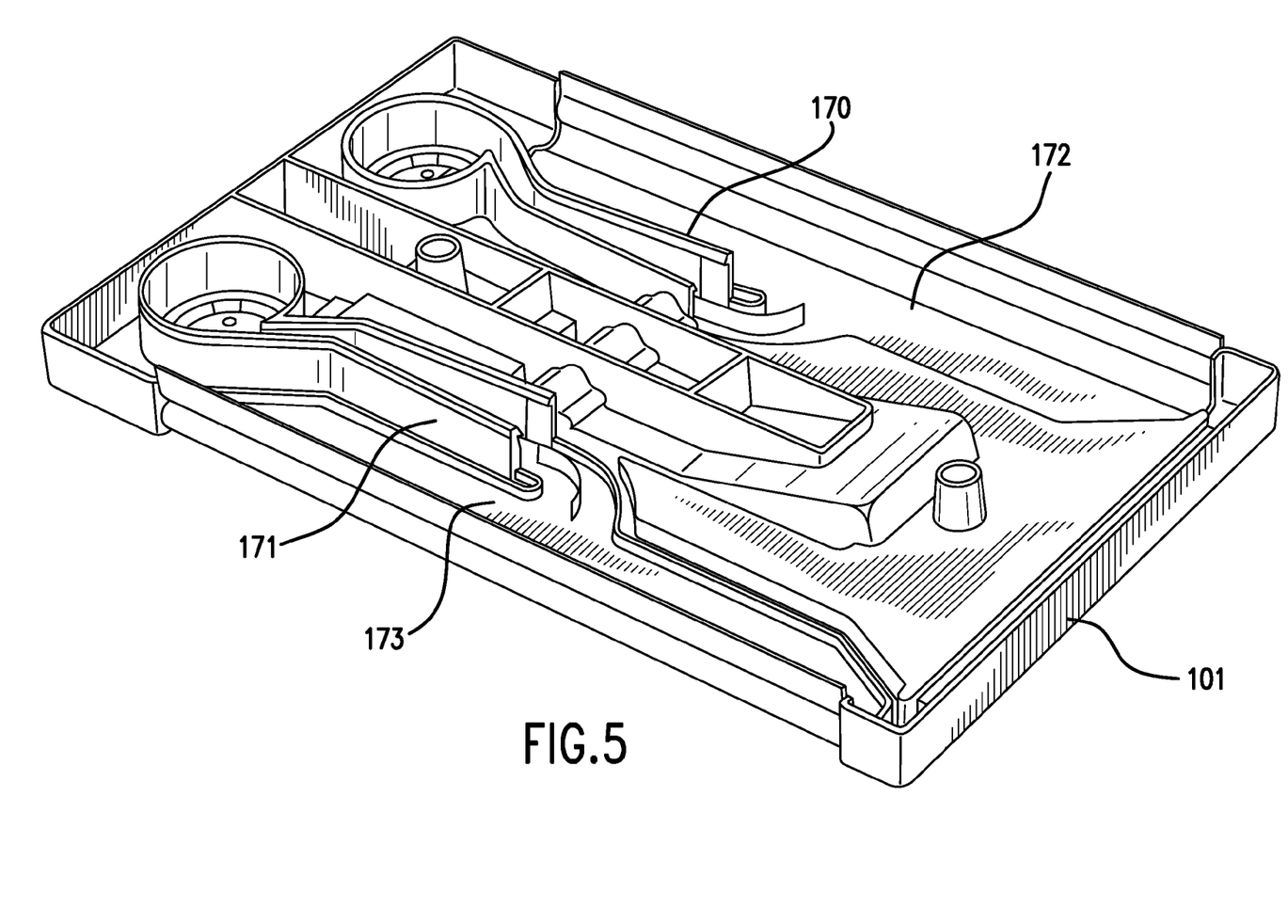
FIG. 5 is a perspective view of the mattress base shown in FIG. 4.

FIG. 5 shows an overhead perspective view of the base member 101. The base member 101 contains two (2) separate volute housings 170, 171 for receiving two (2) separately controlled fan devices (e.g., fan devices 102, 103 discussed above). The volute housings 170, 171 may include heating elements (not shown), disposed in either the walls of the housings themselves, or within the path of the air flow. The fan device associated with each of the volute housings 170, 171 may be separately controlled, so as to allow independent control of air flow to each side of the mattress tray 108 (e.g., the left and right sides). The base member 101 may also contain the lower halves 172, 173 of side air flow channels 182, 183, the upper halves of which are formed by the first and second air circulation members 104, 105. In particular, when first and second air circulation members 104, 105 are placed on top of the base member 101, they combine with the base member to form air flow channels 182, 183 along the sides of the mattress tray assembly 100. These air flow channels 182, 183 can best be seen in FIG. 6, discussed below. The mattress tray assembly 100, and thus each of the air flow channels 182, 183, may be mounted on a central pivot 195 (shown in FIG. 6) which allows fifteen degrees (15°) or more of tilt in either direction about a tilt axis 110 (which may be coaxial with, or substantially parallel to, a longitudinal axis of a humidity inlet 190, described below), so as to allow the air flow to be directed to specific portions of the interior of the chamber formed by the hood 145. Steam can also be supplied to the air flow channels 182, 183 to increase humidity inside the chamber formed by the hood 145.

In operation, air enters the air circulation system through the first nozzle 160 (from the chamber formed under the hood 145), and is drawn towards the first and second fan devices 102, 103 through first and second air flow tubes 165, 166. The first and second fan devices 102, 103 then push the air through the volute housings 170, 171, and into the side air flow channels 182, 183 formed by the sides 172, 173 of the base member 101, and the first and second air circulation members 104, 105. The air then enters the chamber formed under the hood 145, where the patient resides, along the long sides of the base member 101. The air within the chamber formed under the hood 145 is eventually pulled back through the first nozzle 160, and re-circulated. If the air control device 109 associated with the second nozzle 161 is in an 'open' position, air will also flow in a channel along the short wall of the base member 101 (i.e., the end opposite the first nozzle 160), and into the chamber formed under the hood 145. Because the second nozzle is configured so as to direct air towards the first nozzle (as explained below), opening the air control device 109 improves air flow through the air circulation system in most cases.

Figure 6:
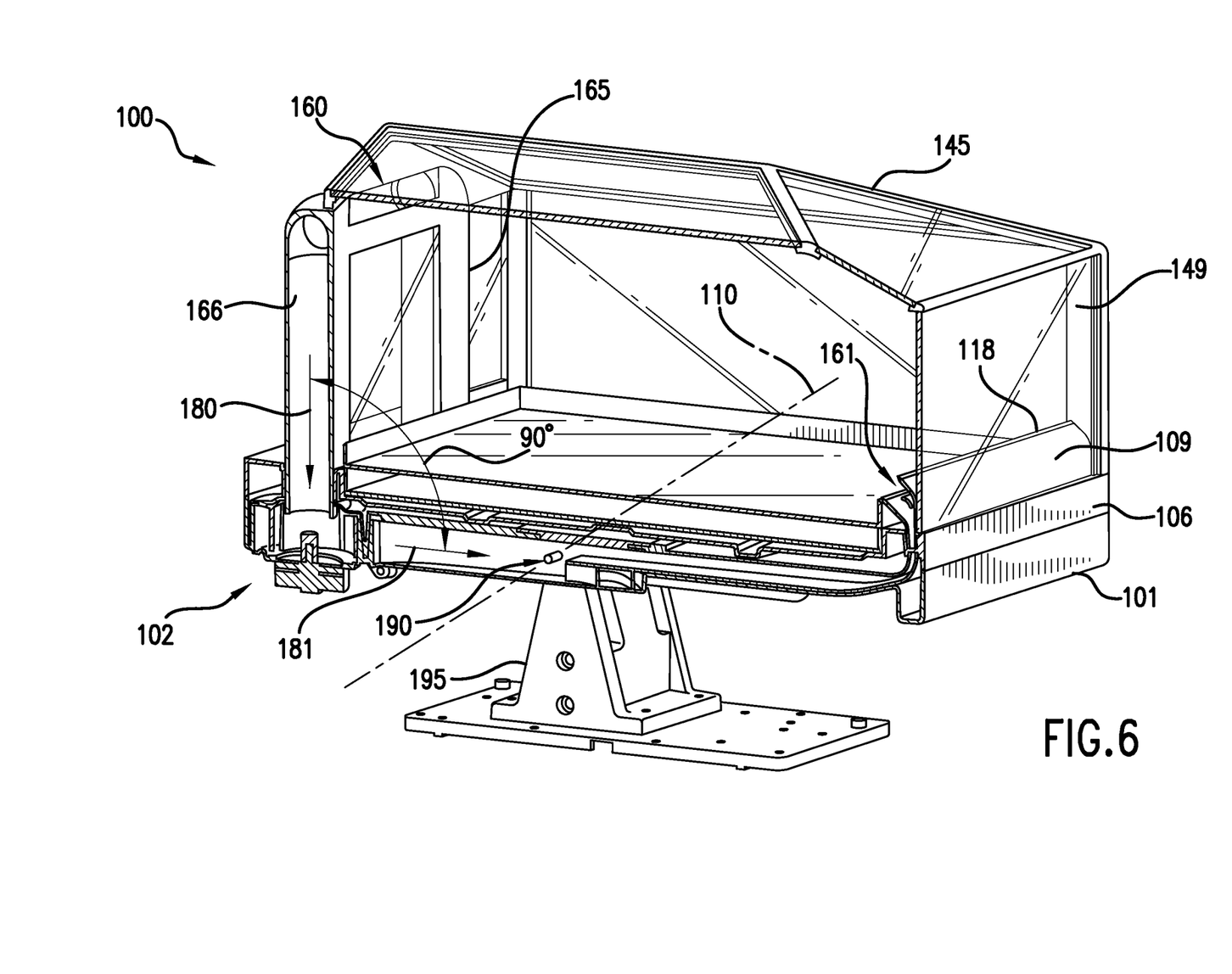
FIG. 6 is perspective partial cross-section view of the mattress tray assembly shown in FIG. 3.

FIG. 6 shows a perspective partial cross-section view of the mattress tray assembly 100 which includes arrows showing the direction of air flow. In particular, the flow enters the first nozzle 160, and is sucked down in respective air flow tubes 165, 166 of the first nozzle 160 in the direction of the first arrow 180. When the air reaches the first air flow device 102, it is subjected to a ninety degree (90°) change in direction, and proceeds in the direction of second arrow 181, through the volute housings 170, 171, and the above-described air flow channels 182, 183 formed by the base member 101 and the first and second air circulation members 104, 105. The air exits into the chamber formed by the hood 145 through side nozzles disposed on the left-hand and right-hand sides of the mattress tray 108. If the air control device 109 is in an 'open' position, air may also enter the chamber formed by the hood 145 through the second nozzle 161. It will be noted that the outer walls of the air control device 109 are angled so as to direct air emanating from the second nozzle back to the first nozzle 160. This orientation of the first and second nozzles 160, 161 assists in the flow of air though the mattress tray assembly 100.

The following design features, which increase device efficiency, and improve usability, are also shown in FIG. 6. First, those of ordinary skill in the art will recognize that air flow coming from the first nozzle 160 needs to make a ninety degree (90°) turn when the flow is pumped under the mattress tray 108. By positioning the fan devices 101, 102 at the point of this turn, device efficiency is increased because the 90° turn achieved in the fan devices, where flow turns anyway. This positioning of the fan devices 102, 103 also simplifies the air flow channel (duct) geometry, which leads to easier cleaning and disassembly of the device. Second, the parts that form the air flow channels 182, 183 formed by the base member 101 and the first and second air circulation members 104, 105 may include overlapping sidewalls, which ensure that the air flow channels 182, 183 are air tight, while also allowing easy opening of the channel for cleaning.

For example, FIGS. 9A and 9B show sidewalls 115 of the base member 101 which are overlapped by the sidewalls 116 of the second air circulation member 105, so that the second air circulation member can be easily coupled to, and decoupled from, the base member. The separate halves of the air flow channels 182, 183 (e.g., the base member 101 and the first and second air circulation members 104, 105) may also include a vertical draft, which allows the halves to be easily assembled, and disassembled for cleaning, as shown in FIG. 9B. Third, the humidity inlet 190 is disposed centrally on the mattress tray assembly 100 (as shown in FIG. 6), along a tilt axis 110 of the mattress tray assembly, allowing easy transmission of the humidity from the humidifier unit (not shown) to the tilted mattress assembly. In other words, the tilt axis 110 may be coaxial with, parallel to, or coplanar with, the longitudinal axis of the humidity inlet 190. Because the humidifier unit is typically disposed with its main axis horizontal to the plane of the mattress tray 108, disposing the humidity inlet 190 along the tilt axis 110 of the mattress tray assembly 100 allows positioning of the humidifier unit on a non-tilting portion of the warming therapy device, and allows easy transmission of steam generated thereby to the tilted mattress tray assembly 100. Fourth and finally, the upper wall 118 of the air control device 109 may include a pivot which permits the air control device to be opened and closed, thereby permitting the second nozzle 161 to be selectively opened and closed. Opening of the air control device 109 may be accomplished, for example, by means of a tension spring (not shown) attached to the upper wall 118 of the second nozzle 161, whereas closing of the air control device 109 may be performed by a rigid or semirigid actuating rod (not shown), or other equivalent means, moving inside a corner piece 149 of the hood 145. The actuating rod may additionally be coupled to the cover portion 146 of the hood 145, so that the air control device 109 opens and closes as the cover portion opens and closes.

Figure 7:
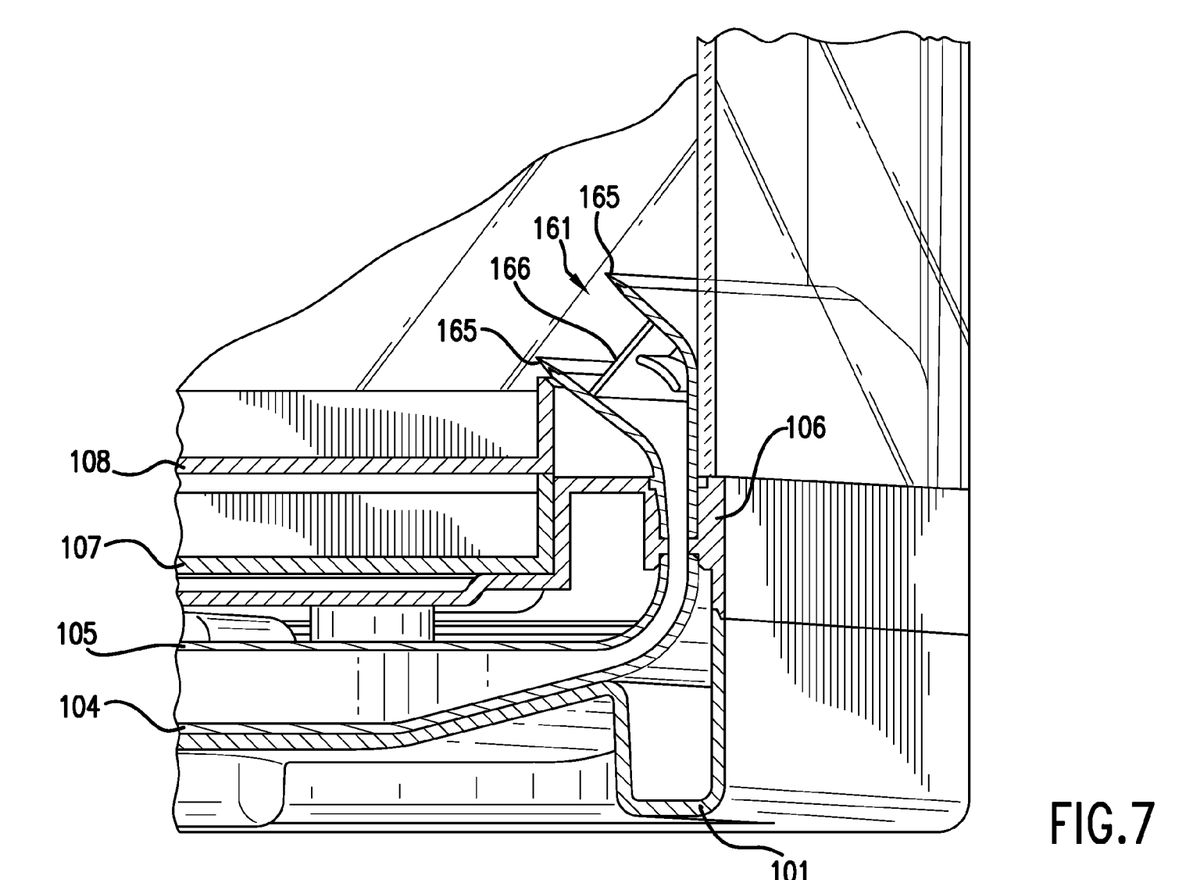
FIG. 7 is a detail view of a portion of the mattress tray assembly shown in FIG. 6.

FIG. 7 shows detailed cross-section of a portion of the mattress tray assembly 100, showing details of the second nozzle 161. As shown, the walls of the second nozzle 161 may include flexible tips 165 which are relatively sharp. Such sharp, flexible tips 165 permit the second nozzle 161 to achieve improved aerodynamic performance, while simultaneously being safe for caregiver and the patient, due to the softness of the material used for the tips (e.g., rubber, etc.). The flexible tips 165 may be manufactured as a separate part which is coupled or attached to the second nozzle 161, or may be over-molded on the second nozzle. Additionally, those of ordinary skill in the art will recognize that such sharp, flexible tips may be used on the side air flow channels 182, 183 (formed by the lower halves 172, 173 of the base member 101 and the first and second air circulation members 104, 105) as well.

As also shown in FIG. 7, the second nozzle 161 may also include a porous or semi-porous flow element 166, in order to make air flow through the nozzle uniform. The flow element 166 may also act as an air filter, preventing entrainment of small objects inside the nozzle. The flow element 166 may be made of polymer mesh, or other equivalent material, and may be made disposable. As noted above with regard to the flexible tips 165, those of ordinary skill in the art will recognize that the flow element 166 may also be used on the side air flow channels 182, 183 (formed by the lower halves 172, 173 of the base member 101 and the first and second air circulation members 104, 105).

Figure 8:
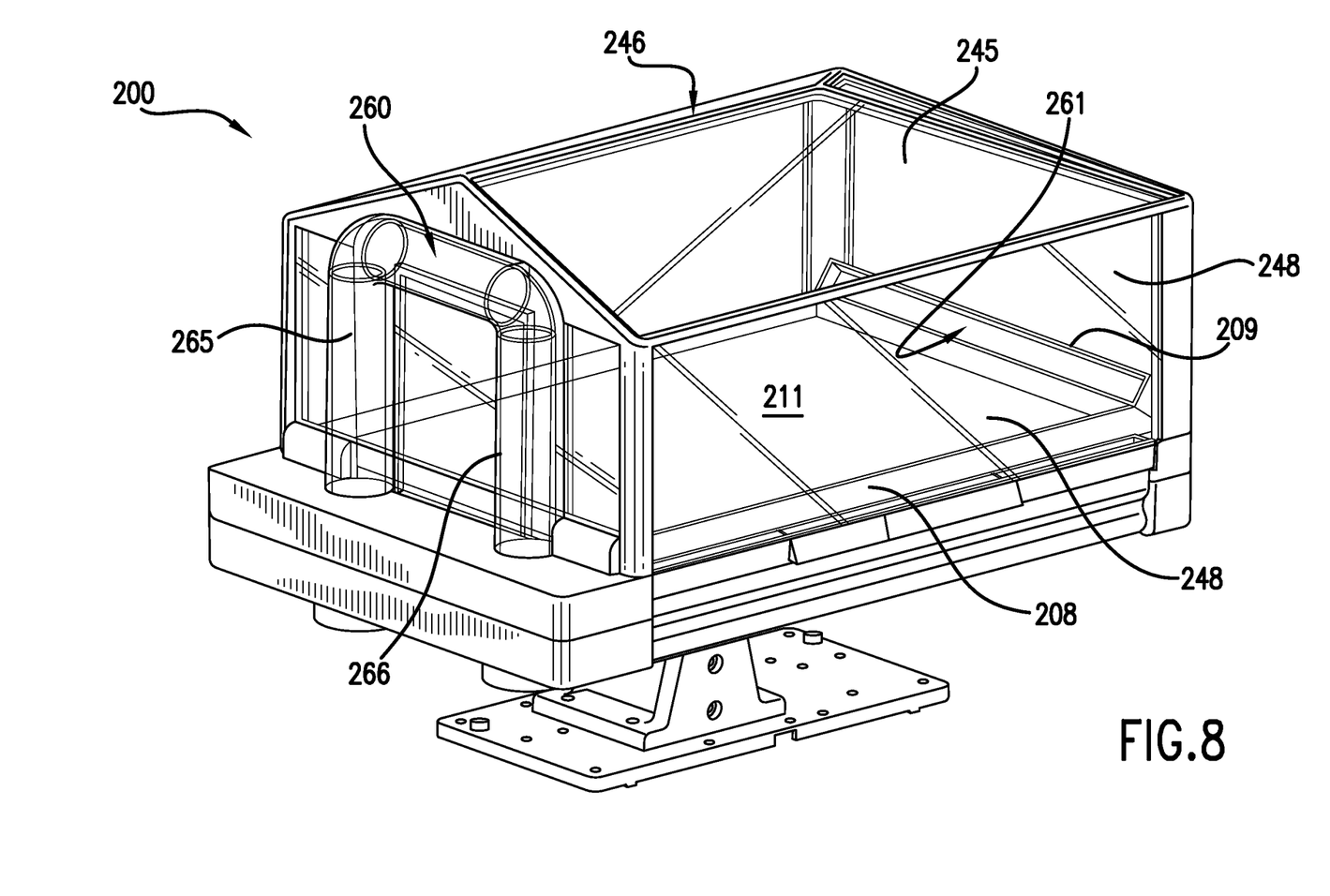
FIG. 8 is a perspective view of a mattress tray assembly according to a second exemplary embodiment of the present invention.

FIG. 8 shows a perspective view of a mattress tray assembly 200 according to a second exemplary embodiment of the present invention. The mattress tray assembly 200 is similar to the mattress tray assembly 100 described above, and like reference numerals denote like elements. The mattress tray assembly 200 includes a hood 245, formed of a top portion 246, and one or more sidewalls 248 which may be slideable, removable, pivotable or rotatable. The mattress tray assembly 200 may also include a mattress tray 208, with a mattress 211 disposed therein. The mattress tray assembly 200 may additionally include a first nozzle 260 disposed under the hood 245 and overlying the mattress tray 208 which acts as an air return. A second nozzle 261 may optionally be disposed at an opposing end of the mattress tray assembly 200 from the first nozzle 260, and may include a means to open and close an air passage to thereby enable and disable air flow through the second nozzle. For example, the first nozzle 260 may be disposed at a head-end of the mattress tray assembly 200, and the second nozzle 261 may be disposed at a foot-end of the mattress tray assembly. The mattress tray assembly 200 may also include an air control device 209. The air control device 209 may comprise a flap or other equivalent means, which may be opened and closed so as to allow air to flow to the second nozzle 261. For example, when the air control device 209 is disposed in a 'closed' position, the nozzle 261 will not be active, but when the air control device is disposed in an 'open' position, the nozzle 261 is active.

One difference with the mattress tray assembly 200 is the use of a first nozzle 260 and air flow tubes 265, 266 which are transparent, semi-transparent or translucent. In the case of a transparent or semi-transparent nozzle, the infant patient is more easily viewed by the caregiver from angle behind the head of the patient. A transparent or semi-transparent nozzle also permits the placement of one or more examination lights and/or phototherapy lights behind the nozzle (as opposed to inside the hood 145, or on a backbone disposed inside the hood). Additionally, a fiber optic or other equivalent light source may be disposed within the nozzle 260, or one or more of the air flow tubes 265, 266, thereby allowing the air flow tubes to act as an independent light source. Particularly, the air flow tubes 265, 266 would have the appearance of low intensity neon light, which could operate as a 'night light' for the infant patient, if so desired.

As will be noted by those of ordinary skill in the art, the mattress tray assemblies 100, 200 according to the first and second exemplary embodiments may be integrated into a warming therapy device such as the device 10 shown in FIG. 1. For example, the mattress tray assemblies 100, 200 may be formed on a movable patient support assembly (e.g., patient support assembly 30) which includes a radiant heater (e.g., radiant heater head 20).

Further, although the mattress tray assemblies 100, 200 according to the first and second exemplary embodiments are shown and described above with reference to an associated warming therapy device 10 of a specific configuration, those of ordinary skill in the art will realize that the mattress tray assemblies 100, 200 may be integrated into any suitable incubator, warmer, medical treatment device or other equivalent apparatus. Further, although the mattress tray assemblies 100, 200 are described above with reference to air or oxygen comprising the circulated gas, those of ordinary skill in the art will realize that any gas may be heated and circulated using the mattress tray assemblies 100, 200 without departing from the scope of the present invention.

Although an exemplary embodiment of the present invention has been described above for use in procedures involving infant patients, those of ordinary skill in the art will realize that the warming therapy device 10, and mattress tray assemblies 100, 200, according to the exemplary embodiments of the present invention, may be used for other types of operations and procedures, including for children and adults without departing from the scope of the present invention.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An apparatus comprising:
a patient support assembly; and,
an air circulation system coupled to the patient support assembly, said air circulation system including first and second air flow channels which are separate from one another,
wherein the first air flow channel includes a first fan device and the second air flow channel includes a second fan device, such that the air flow through the first and second air flow channels may be separately controlled, and wherein the first air flow channel includes a first volute housing disposed therein, and the second air flow channel includes a second volute housing disposed therein.

2. The apparatus of claim 1, further comprising a mattress tray assembly coupled to the patient support assembly, the air circulation system forming part of the mattress tray assembly.

3. The apparatus of claim 2, wherein the first air flow channel is formed on a first side of the mattress tray assembly and the second air flow channel is formed on a second opposing side of the mattress tray assembly.

4. The apparatus of claim 1, wherein the air circulation system includes a first nozzle which acts as an air return.

5. The apparatus of claim 4, wherein the first nozzle is coupled to first and second air flow tubes.

6. The apparatus of claim 5, wherein the first air flow tube is coupled to the first air flow channel, and the second air flow tube is coupled to the second air flow channel.

7. The apparatus of claim 1, wherein each of the first and second air flow channels are formed of first and second air circulation members.

8. The apparatus of claim 1, the air circulation system additionally including an air control device and a first nozzle, wherein the air control device may be configured to direct air towards the first nozzle, which acts as an air return.

9. The apparatus of claim 8, wherein the air control device includes at least one flow element.

10. The apparatus of claim 1, wherein at least one of the air flow channels is formed of a base member, a first air circulation member and a second air circulation member.

11. The apparatus of claim 5, wherein the first and second air flow tubes are transparent.

12. The apparatus of claim 1, wherein the air circulation system includes at least one nozzle including a porous flow element.

13. The apparatus of claim 1, wherein the first fan device is disposed at a turn of the first air flow channel.

14. The apparatus of claim 1, wherein the air circulation system includes at least one nozzle including a flexible tip.

15. The apparatus of claim 2, wherein the air circulation system includes at least one humidity inlet with a longitudinal axis disposed substantially parallel to a tilt axis of the mattress tray assembly.

16. An apparatus comprising:
a patient support assembly; and,
an air circulation system coupled to the patient support assembly, said air circulation system including first and second air flow channels which are separate from one another,
wherein the first air flow channel includes a first fan device and the second air flow channel includes a second fan device, such that the air flow through the first and second air flow channels may be separately controlled,
wherein each of the first and second air flow channels are formed by the combination of a base member, a first air circulation member, and a second air circulation member, such that at least one wall of the second air circulation member overlaps at least one wall of the base member, and wherein the base member includes first and second volute housings formed therein, the first volute housing corresponding to the first air flow channel, and the second volute housing corresponding to the second air flow channel.

\* \* \* \* \*